United States Patent [19]

Larcher

[11] Patent Number: 4,947,870

[45] Date of Patent: Aug. 14, 1990

[54] ACROMIOCLAVICULAR SUPPORT

[76] Inventor: Angelo C. Larcher, 8036 S. Western Ave., Chicago, Ill. 60620

[21] Appl. No.: 161,113

[22] Filed: Jun. 6, 1988

[51] Int. Cl.$^5$ .......................... A61F 5/04; A61F 5/00
[52] U.S. Cl. ..................................... 128/875; 128/78; 128/87 R; 128/94; 128/876; 128/869; 128/DIG. 19; 2/310
[58] Field of Search .................. 2/268, 326, 327, 328, 2/269, 267, 310, 333; 128/102.1, 105.1, 106.1, 107.1, DIG. 19, 77, 78, 87 R, 94, 876, 873–875, 878, 888–889, 869; 224/907, 264, 257, 242

[56] References Cited

U.S. PATENT DOCUMENTS

| 201,597 | 3/1878 | Cushman | 2/328 |
|---|---|---|---|
| 1,288,170 | 12/1918 | Pick | 1/1 |
| 1,404,719 | 1/1922 | Postl | 2/326 |
| 1,638,304 | 8/1927 | Guy | 2/326 |
| 1,697,363 | 1/1929 | Losey | 128/875 X |
| 1,816,262 | 7/1931 | Ritter | 128/875 X |
| 2,185,400 | 1/1940 | Cohen | 2/334 |
| 2,483,809 | 10/1945 | Clark et al. | 2/268 |
| 2,497,808 | 2/1950 | Zacks | 2/268 |
| 2,532,059 | 11/1950 | Dee | 2/268 |
| 2,534,513 | 12/1950 | Gerry | 2/268 |
| 2,624,885 | 1/1953 | MacManus | 2/268 |
| 2,627,368 | 2/1953 | Jantzen | 2/268 |
| 2,640,993 | 6/1953 | Kleinman | 2/268 |
| 2,676,328 | 4/1954 | Skirow et al. | 2/268 |
| 2,727,247 | 12/1955 | Bailey . | |
| 3,050,734 | 8/1962 | Dopyera | 2/268 |
| 3,184,883 | 5/1965 | McCook | 46/32 |
| 3,188,090 | 6/1965 | Job | 128/878 X |
| 3,897,776 | 8/1975 | Gaylord, Jr. | 128/DIG. 19 |
| 4,188,944 | 2/1980 | Augustyniak | 128/94 |
| 4,198,964 | 4/1980 | Honneffer | 128/44 |
| 4,480,637 | 11/1984 | Florek | 128/94 |
| 4,491,129 | 1/1985 | Lockwood | 128/94 |
| 4,550,869 | 11/1985 | Johnson | 128/94 |
| 4,589,406 | 5/1986 | Florek | 128/87 R |
| 4,654,893 | 4/1987 | Meyers et al. | 2/2 |
| 4,751,923 | 6/1988 | Marino | 128/878 |
| 4,784,128 | 11/1988 | Schevermann | 2/310 X |
| 4,878,490 | 11/1989 | Scott | 128/77 |

FOREIGN PATENT DOCUMENTS

| 500684 | 2/1951 | Belgium | 2/326 |
|---|---|---|---|
| 1350503 | 12/1963 | France | 128/875 |
| 133641 | 6/1929 | Switzerland | 128/DIG. 19 |
| 403258 | 12/1953 | United Kingdom | 2/326 |

Primary Examiner—Werner H. Schroeder
Assistant Examiner—Jeanette E. Chapman
Attorney, Agent, or Firm—Martin Faier

[57] ABSTRACT

An acromioclavicular support intended to provide sufficient pressure upon an acromioclavicular separation of a patient to permit the separation to heal, wherein the support includes an abdominal belt adapted for wearing around the patient's waist and having front and rear sides, a shoulder pad adapted for seating over the acromioclavicular separation, step connectors on opposed sides of the shoulder pad, a pair of straps one slidebly connected to the front side of the abdominal belt and the other slideably connected to the rear side of the adominal belt, each of said straps extending from said abdominal belt through its respective correcsponding strap connector and having a free end anchored to said abdominal belt spaced apart from its point of slidble onnection to said abdominal betl, each of said straps haing a buckle for tightening amd loosening said strap to apply pressue over said acromioclavicular separation through the shoulder pad.

18 Claims, 2 Drawing Sheets

ACROMIOCLAVICULAR SUPPORT

BACKGROUND AND SUMMARY OF THE INVENTION

This invention related to shoulder supports and is more particularly directed to an acromioclavicular support for humans, particularly useful in treating and retaining in position most degrees of ligamentous ruptures.

Typically, there are three degrees of acromioclavicular (hereinafter referred to as "a/c") sprains:

(1) first degree, where there is a very slight tearing of the a/c ligamentous fibers, resulting in localized pain over the a/c joint;

(2) second degree, where there is a greater tearing of these a/c ligaments and greater disability and more substantial pain upon motion; and (3) third degree, where there is severe ligamentous sprain in which one or more of the ligaments have been completely ruptured or torn, and there is dislocation of the clavicular.

In each of these degrees of a/c sprain, the clavicle is in misalignment with the acromion and the ligaments therebetween are injured, from mere misalignment of the first degree, where there is slight separation but the shoulder parts are still co-planar, to the second degree, where there is partial separation and the clavicle and acromion are out of alignment and the shoulder parts are no longer co-planar, and to the third degree, where there is complete separation and misalignment of the clavicle and the acromion.

Frequently, these conditions, which often result from sports injuries, are treated surgically, because treatment requires long term healing, and sometimes relatively complete immobility, for six weeks or more. Such surgical procedures often result in a stiff shoulder because a pin is inserted in the shoulder joint or a fusion of the joint is made to hold the a/c in position relative to the clavicle.

Only careful and patient tending to these injuries can allow recovery, because of the need to immobilize the shoulder during healing and to apply specific pressure to the a/c for a relatively long term. Known supports do not have the ability to draw the a/c to the clavicle. Such supports may be too high on the shoulder or they may slip out of position or they are not suitable for long term wear or they apply improper pressure to one side or the other of the joint.

The support embodying the present invention provides a firm fixation of the a/c articulation and retains the a/c dislocation and its sprain in anatomical apposition. Such a preferred support will maintain sufficient pressure upon the a/c separation to retain the sprained area in healing configuration. The preferred support will not immobilize the shoulder girdle completely or as a result cause atrophy and weakness of the girdle muscles to occur during immobilization.

A preferred a/c support following the teachings of the present invention has an abdominal belt and straps, one end of each of which is slidably connected to the belt, which rise from the front and rear sides of the belt and are adjustably secured to a pad dimensioned for covering the a/c joint, and the free end or distal portion of each strap is secured to the belt by means of an adjustable buckle spaced apart from the other distal strap slidable connection end. Through such a device, the pad is maintained under sufficient pressure to heal the a/c joint, because the straps may be adjusted to properly distribute belt pressure upon the shoulder pad and to provide tension of the shoulder pad upon the separated a/o articulation and retain its apposition.

The support embodying the present invention is not for use on a fracture of the clavicle or for sterno clavicular separation, but is intended for use strictly in a/c separations where distributed downward pressure and tension from the front and rear of the patient can promote healing of the a/c joint.

Adjustable straps also permit the strap lengths to be changed as necessary for use with patients of greater or lesser height or more or less abundant structure, giving the support embodying the present invention great versatility for reuse by different persons.

OBJECTS AND ADVANTAGES OF THE INVENTION

It is the object of the invention to provide a novel acromioclavicular support of the character described.

Another object is to provide a novel a/c support for a human which includes an abdominal belt along which straps for connecting a pad to the belt may be attached to provide adjustable downward tension of the pad when placed over an a/c sprain to distribute pressure on the a/c joint of the wearer.

Another object is to provide a novel pad and connection means for applying distributed pressure to the a/c joint of a wearer.

Another object is to provide novel support means for distributing tension of a pad on the a/c joint of a human.

Another object is to provide novel adjustment means for an a/c support which adapted to apply and maintain pressure on an a/c sprain.

Another object is to provide adjustable straps and means for adjusting an a/c shoulder support.

Another object is to provide an a/c support which is easy and economical to manufacture, and which is effective in treating a/c sprains, without causing undue discomfort to the wearer.

DESCRIPTION OF A PREFERRED EMBODIMENT

Figure 1:
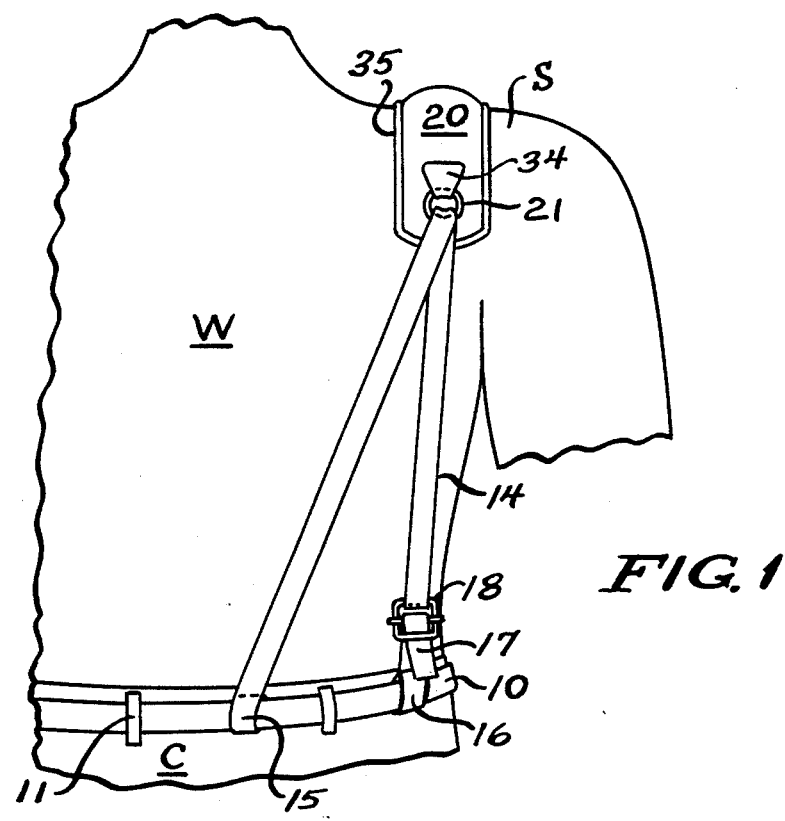
FIG. 1 is a partial rear elevational view showing the a/c support embodying the present invention in position on a wearer.
Figure 2:
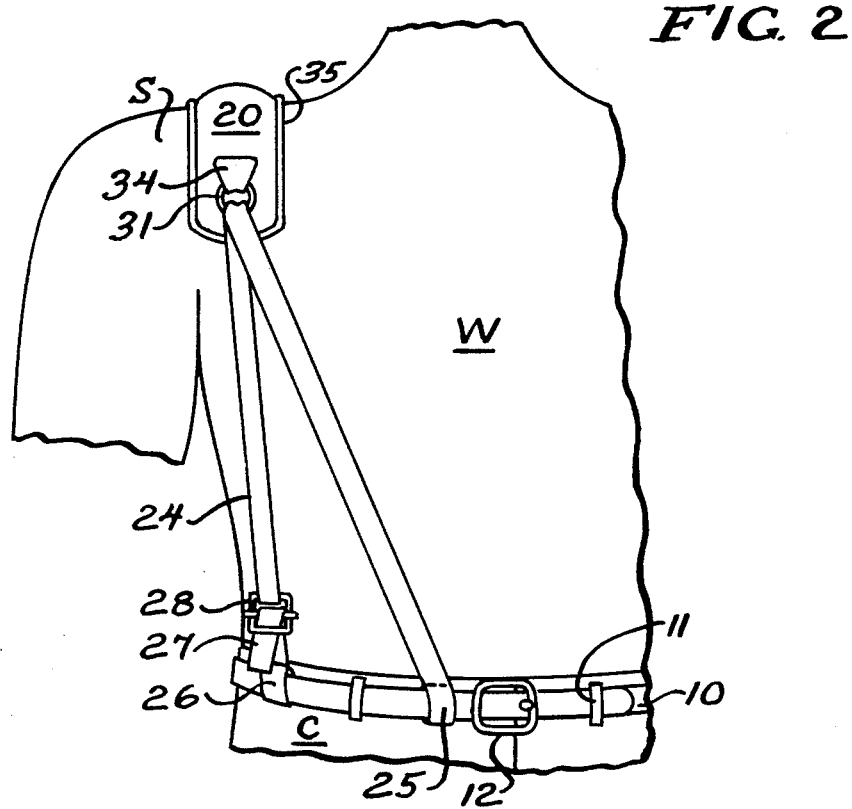
FIG. 2 is a partial front elevational view of the a/c support shown in FIG. 1.
Figure 3:
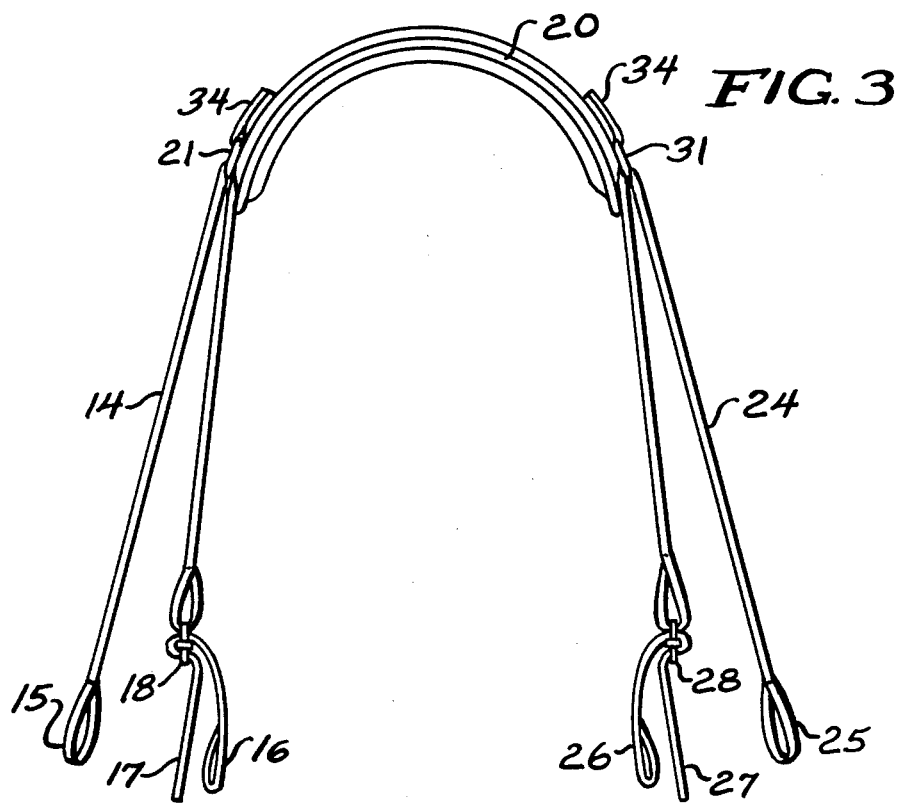
FIG. 3 is a side elevational view of the novel a/c support, with the abdominal belt omitted.
Figure 4:
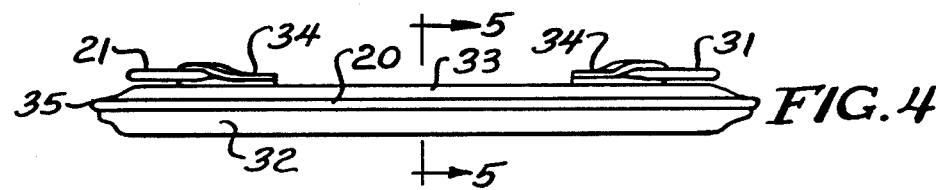
FIG. 4 is a side elevational view of an a/c shoulder pad for use in the present invention.
Figure 5:
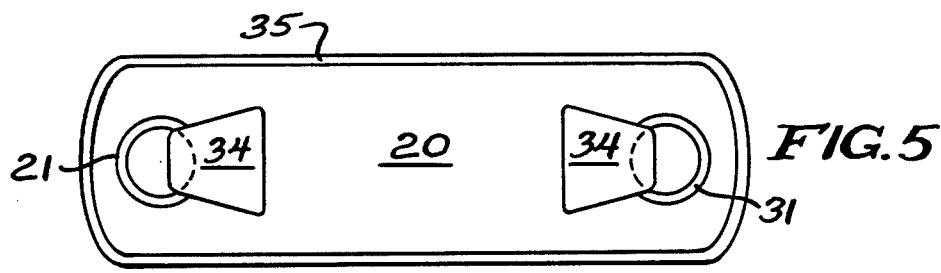
FIG. 5 is a top view of the a/c shoulder pad shown in FIG. 4.
Figure 6:
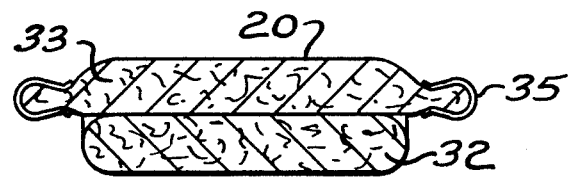
FIG. 6 is a sectional view of the a/c shoulder pad shown in FIG. 4, taken on line 5—5, with the pulley ring omitted.

An acromioclavicular support embodying the present invention is intended to be worn of the shoulder S of a wearer W over the a/c joint, as shown in FIGS. 1 and 2.

This support preferably has an abdominal belt 10, which may be fed through belt loops 11 of clothing C of the wearer, and the belt may be closed by a buckle 12.

On the rear side of the belt 10, as shown in FIG. 1, extending from the belt is a strap 14, which at one end is slideably connected to the belt by means of a first loop 15, which may be formed by sewing or otherwise connecting the end of the strap to the belt. The other end of the strap 14 is also connected to the belt by means of a second loop 16 in a short strap 17 having a cinch buckle 18. A pad 20 is placed over the a/c joint on the shoulder S of the wearer, which has a pulley ring 21, and the strap 14 is inserted therethrough.

As shown in FIG. 2, on the front side of the belt 10, extending from the belt is another strap 24, which at one end is slideably connected to the belt by means of a first loop 25, and the other end of the strap is also connected to the belt by means of a second loop 26 in a short strap 27 having a cinch buckle 28. The pad 20 has another pulley ring 31, through which the strap 24 is connected.

The pad 20 preferably has two layers of material. The first layer 32 is of densely compressed soft cotton fiber which may be enclosed in a sock and is intended to be worn adjacent the a/c joint. The second layer 33 is of less dense spongy material, and has sewn to its top surface the pulley rings 21 and 31, which may be connected by means of lengths of webbing 34. Around the edge of this second layer is a length of welting 35, and its ends but preferably not its sides, may be secured to the dense layer 32. This pad 20 must be flexible, but firm, to suitably support the a/c joint, and is preferably of a non-irritating material to the human skin.

In use, the pad 20 is placed over the a/c joint in position with the front and back straps 14 and 24 suitably connected to the belt, as shown in FIGS. 1 and 2. The short straps 17 and 27 are drawn up through the respective cinch buckles 18 and 28, self-adjusting through the respective rings 21 and 31 to draw the pad 20 down over the a/c joint on the shoulder, where they will remain until the cinch buckles 21 and 31 are released. The flexible but firm construction of the pad and the preferably web-like material of the straps and the ring connections 34 provide sufficient resiliency to the support to maintain the pad in position for retaining the acromioclavicular joint suitably immobilized together for healing, without adversely affecting or immobilizing other shoulder ligaments, tendons and bones.

While a preferred embodiment of the invention has been disclosed for purposes of illustration, it should be understood that many changes and variations in the details and specific combinations shown and described can be made without departing from the spirit or scope of the invention. Accordingly, it is not desired that the invention should be limited to the combinations and structure disclosed.

I claim:

1. A shoulder support for providing downward pressure upon an acromioclavicular separation of the shoulder of a wearer to substantially immobilize and permit healing of an acromioclavicular joint, said support comprising a shoulder pad adapted for seating over the shoulder extending from front and back of a wearer, strap connecting means on opposite sides of said pad, and strap means for the front and back of said wearer extending from said strap connecting means to a lateral member adapted for connecting said strap means around the torso of the wearer, said strap means being adjustable to draw said pad under tension toward said lateral member for securely holding said pad over said joint, said strap means are slidably securable on said lateral member.

2. The shoulder support recited in claim 1, wherein said strap connecting means comprises like strap connectors, one adapted for securement at the front of said wearer and the other adapted for securement at the rear of said wearer.

3. The shoulder support recited in claim 1, wherein said strap means are movably secured in said strap connectors.

4. The shoulder support recited in claim 1, wherein each of said strap means has distal ends securable on said lateral member, and each of said distal ends has a loop through which said lateral member extends.

5. The shoulder support recited in claim 1, wherein said strap means has a short strap which is connectable to said lateral member.

6. The shoulder support recited in claim 1, wherein said strap means has strap adjusting means for shortening or lengthening said strap means.

7. The shoulder support recited in claim 6, wherein said strap adjusting means has a cinch buckle for locking and unlocking said strap means in selected position.

8. The shoulder support recited in claim 6, wherein adjustment of said strap adjusting means causes movement of said strap means from said lateral member through said strap connecting means.

9. A shoulder support for providing downward pressure upon an acromioclavicular separation of the shoulder of a wearer to substantially immobilize and permit healing of an acromioclavicular joint, said support being adapted for connection to a lateral member adapted for encircling the waist of a wearer, said support comprising a shoulder pad adapted for seating over the shoulder extending from front and back of a wearer, strap connecting means or opposite sides of said pad, and adjustable strap means for the front and back sides of said wearer connecting said strap connecting means to said lateral member for drawing said pad downwardly over said joint under tension toward said lateral member, the said strap means on each of said sides extended from said pad forming a continuous loop and the ends of said strap means adapted for connection to said lateral member being spaced apart.

10. The shoulder support recited in claim 9, wherein said pad has a layer of material adapted for non-irritating contact on the skin which is firm and of compressed fibers, and another layer of material which is flexible to which said strap connecting means are attached.

11. The shoulder support recited in claim 9, wherein said strap means comprises a pair of straps, one adapted for connecting said pad and said lateral member on the front of the wearer and the other adapted for connecting said pad and said lateral member on the back of the wearer.

12. The shoulder support recited in claim 11, wherein each of said straps has distal ends and a central portion passing through and adjustably secured to said strap connecting means.

13. The shoulder support recited in claim 11, wherein said distal ends are connectable spaced apart to said lateral member.

14. The shoulder strap recited in claim 12, wherein one of said distal ends is substantially vertically aligned with said pad when in support position on the wearer.

15. The shoulder strap recited in claim 13, wherein another of said distal ends is angular disposed to said vertically aligned distal end.

16. The shoulder strap recited in claim 14, wherein said vertically aligned distal end of said strap has adjustably securable means for tightening said pad over said joint.

17. The shoulder strap recited in claim 9, wherein said strap means are connected to said pad applying such tension on the sides of the top of said pad remote from the shoulder of the wearer.

18. The shoulder strap recited in claim 17, wherein said pad is flexible in the direction of the front and back of the wearer and held in tension in a vertical direction over said joint when adjusted toward said lateral member.

* * * * *